US011814334B2

(12) United States Patent
Näsholm et al.

(10) Patent No.: US 11,814,334 B2
(45) Date of Patent: Nov. 14, 2023

(54) SEPARATION OF BASIC AMINO ACIDS (71) Applicant: AREVO AB, Umeå (SE)

(72) Inventors: Torgny Näsholm, Umeå (SE); Jonathan Love, Umeå (SE); Mattias Holmlund, Umeå (SE); Nils Bertil Skoglund, Vännäsby (SE)

(73) Assignee: AREVO AB, Umeå (SE)

(*) Notice: Subject to any disclaimer, the term of this patent is extended or adjusted under 35 U.S.C. 154(b) by 160 days.

(21) Appl. No.: 16/976,918

(22) PCT Filed: Mar. 5, 2019

(86) PCT No.: PCT/SE2019/050188
§ 371 (c)(1),
(2) Date: Aug. 31, 2020

(87) PCT Pub. No.: WO2019/172825
PCT Pub. Date: Sep. 12, 2019

(65) Prior Publication Data
US 2021/0017122 A1 Jan. 21, 2021

(30) Foreign Application Priority Data
Mar. 5, 2018 (SE) .................... 1850233-6

(51) Int. Cl.
*C07C 227/42* (2006.01)
*C05B 15/00* (2006.01)
*C07C 277/08* (2006.01)

(52) U.S. Cl.
CPC ............ *C07C 227/42* (2013.01); *C05B 15/00* (2013.01); *C07C 277/08* (2013.01)

(58) Field of Classification Search
None
See application file for complete search history.

(56) References Cited

U.S. PATENT DOCUMENTS

| | | | |
|---|---|---|---|
| 4,006,004 A | 2/1977 | Seferian et al. | |
| 5,312,980 A | 5/1994 | Yonsel et al. | |
| 9,682,026 B2 | 6/2017 | Kohli et al. | |
| 2009/0281347 A1* | 11/2009 | Tachiya | C07C 227/18 560/37 |
| 2009/0291477 A1 | 11/2009 | Kishino et al. | |

FOREIGN PATENT DOCUMENTS

| | | |
|---|---|---|
| EP | 0175309 A2 | 3/1986 |
| EP | 1792984 A1 | 6/2007 |
| GB | 1245914 A | 9/1971 |
| WO | 2017/200468 A1 | 11/2017 |
| WO | 2017/222464 A1 | 12/2017 |

OTHER PUBLICATIONS

Zhu, Guangyong et al., A review of amino acids extraction from animal waste biomass and reducing sugars extraction from plant waste biomass by a clean method, Biomass Conv. Bioref., vol. 5, pp. 309-320 (2015).

Utagawa, Takashi, Production of Arginine by Fermentation, American Society for Nutritional Sciences, pp. 2854S-2857S (2004).

* cited by examiner

*Primary Examiner* — Sudhakar Katakam
*Assistant Examiner* — Jennifer C Sawyer
(74) *Attorney, Agent, or Firm* — Porter Wright Morris & Arthur LLP (57) ABSTRACT

The present invention relates to a method of separating amino acids from an aqueous solution comprising amino acids as well as proteins and/or protein decomposition products by combining phosphoric acid with the aqueous solution to precipitate an amino acid monophosphate. The precipitate so formed may be separated from the aqueous solution and used as such, e.g. in plant fertilizer compositions. The precipitate may be redissolved in a suitable liquid, after which phosphate and amino acid may be separated following conventional methods. In either case, the present invention enables highly selective precipitation of arginine and/or lysine monophosphate as crystals.

16 Claims, 10 Drawing Sheets

SEPARATION OF BASIC AMINO ACIDS

TECHNICAL FIELD

The present invention relates to the area of amino acid production. More specifically, the invention relates to a method of selectively separating basic amino acids from complex liquids including large number of different proteinaceous and/or nutritional components. Amino acids separated according to the invention are useful e.g. as slow release fertilizers of plants, as food ingredients or as feed additives.

BACKGROUND

Amino acids are organic compounds containing amine (—$NH_2$) and carboxyl (—COOH) functional groups, along with a side chain (R group) specific to each amino acid. The key elements of an amino acid are carbon (C), hydrogen (H), oxygen (O), and nitrogen (N), although other elements are found in the side chains of certain amino acids. Because of their biological significance, amino acids are important in nutrition and are commonly used in nutritional supplements, fertilizers, and food technology. Industrial uses include the production of drugs, biodegradable plastics, and chiral catalysts.

U.S. Pat. No. 4,006,004 (Seferian et al) relates to a phosphate enriched peat moss fertilizer. More specifically, a method for the production of free amino acid-containing phosphate-enriched high organic content fertilizers may include slurrying peat moss in up to five parts by weight of water per part of peat moss, mixing acid phosphate reactant solution of one part by weight of monopotassium acid phosphate with from one to four parts of orthophosphoric acid with the peat moss slurry in an amount of one to four parts by weight of the acid phosphate reactant per part of peat moss, heating the resulting mixture at about 90° C. for not less than 4 hours to hydrolyze proteinaceous material in the peat moss into free amino acid, and recovering as product a peat moss fertilizer containing free amino acid, and enriched with phosphate and potassium. As the phosphoric acid reactant, orthophosphoric acid is preferred, particularly in its commercial form i.e. 85 percent $H_3PO_4$ in aqueous solution. The acid phosphate salt reactant may be an alkali metal i.e. potassium, sodium, lithium, or cesium metal, mono- or di-acid salt. The patent suggests that the hydrolysis of proteinaceous material within peat moss produces usable free amino acids in the product while apparently similar processes do not, by virtue of the conjoint presence of both phosphoric acid and a complimentary phosphate salt such that the pH of the acid is buffered to approximately 25% to 50 percent higher than the acid per se whereby hydrolysis proceeds even at the elevated temperatures and for the prolonged heating periods in such manner as to provide by virtue of the buffered hydrolysis such amino acids as cysteine phosphate, arginine phosphate, alanine phosphate, glycine phosphate, and histidine phosphate, and others.

More recently, WO 2017/200468 (SweTree Nutrition AB) has suggested fertilizer compositions comprising mono-phosphates of basic L-amino acids, such as arginine or lysine monophosphate. The experimental part teaches how crystals of arginine monophosphate can be prepared from a supersaturated solution of arginine phosphate to which an equimolar amount of orthophosphoric acid was added. The solution temperature was increased to about 80° C., and the arginine phosphate solution was slowly cooled at a rate of approximately 5° C./hour. Crystal growth continued as the temperature decreased further. After reaching a temperature of 5° C., the remaining mother liquor was poured off. The crude crystals were dried by vacuum filtration followed by drying in a heat cabinet at 35° C. for approximately 24 hours.

U.S. Pat. No. 9,682,026 (Colgate-Palmolive) relates to an oral care composition comprising arginine phosphate; sodium monofluorophosphate; and dicalcium phosphate dihydrate, which composition is substantially free of organic phosphates. A method of producing such an oral care composition is disclosed, which method comprises the steps of combining together a basic amino acid component, a soluble fluoride salt and a calcium salt of an inorganic acid. For increasing the stability of the fluoride in the composition, the basic amino acid is neutralized with an inorganic acid to form a salt of the basic amino acid prior to the combining step.

In industrial settings, when amino acids are produced through microbial fermentation, a number of separation steps are required in order to obtain a purified product. For example, Utagawa described (Takashi Utagawa in American Society for Nutritional Sciences, p 2854-2857: Production of Arginine by Fermentation (2004)) a process where L-arginine was produced in a process where the fermentation broth required the steps of filtration, cation exchange, anion exchange and de-coloration followed by ultrafiltration, concentration, crystallization and drying. Such process steps require resource in terms of material, manning and time and consequently result in an expensive way of preparing amino acids.

EP 0 175 309 (Toray Industries, Inc) relates to L-lysine production, and more specifically to mutants which are capable of producing high yields in conventional fermentation processes. The high yields are obtained due to the mutants being resistant to one or more α-substituted amino-epsilon-caprolactam compounds. Depending on the medium, it is stated that L-lysine is directly obtainable in the form of crystals from the medium.

Despite the above, there is still a need in this field for improved methods for amino acid production, especially for the production of basic L-amino acids of high purity and with high recovery when prepared from complex solutions.

SUMMARY OF THE INVENTION

One objective of the present invention is to provide an improved method for the manufacture of basic L-amino acids such as arginine or lysine by microbial fermentation, which method simplifies the currently used method by replacing a plurality of purification steps with a single step of precipitation the amino acids. More specifically, this objective may be achieved by a method of separating arginine or lysine from an aqueous solution, which method comprises at least the steps of
a) providing an aqueous solution comprising amino acids as well proteins and/or protein decomposition products;
b) combining the aqueous solution with phosphoric acid;
c) maintaining the aqueous solution including phosphoric acid at room temperature until a precipitate of amino acid phosphate is obtained;
d) separating said precipitate from the aqueous solution; and
e) redissolving the separated precipitate into an aqueous solution of amino acid and phosphate;
wherein the amino acid phosphate is selectively precipitated as a monophosphate of arginine or lysine.

Another objective of the present invention is to provide an efficient method for the production of phosphates of basic amino acids such as arginine or lysine from liquids that comprises amino acids and also have a complex content of proteinaceous components, such as proteins and/or protein decomposition products.

More specifically, this may be achieved by a method of separating arginine or lysine from an aqueous solution, which method comprises at least the steps of
a) providing an aqueous solution comprising amino acids as well as proteins and/or protein decomposition products;
b) combining the aqueous solution with phosphoric acid;
c) maintaining the aqueous solution including phosphoric acid at room temperature until a precipitate of amino acid phosphate is obtained; and
d) separating said precipitate from the aqueous solution; wherein the amino acid phosphate is selectively precipitated as a monophosphate of arginine or lysine.

Other objectives, details and advantages of the present invention may be obtained as defined by the dependent claims, as will be discussed in greater detail in the specification that follows.

BRIEF DESCRIPTION OF THE DRAWINGS

FIGS. 1a, b and c are photographs of three different arginine monophosphate crystals derived according to the invention from different fermentation broths: *Agrobacterium* (FIG. 1a), *E. coli* (FIG. 1b) and *Corynebacterium* (FIG. 1c).

DETAILED DESCRIPTION OF THE INVENTION

The present invention relates to a general method of separating basic amino acids such as arginine or lysine from an aqueous solution, which method comprises at least the steps of
a) providing an aqueous solution comprising amino acids as well as proteins and/or protein decomposition products;
b) combining the aqueous solution with phosphoric acid;
c) maintaining the aqueous solution including phosphoric acid at room temperature until a precipitate of amino acid phosphate is obtained;
d) separating said precipitate from the aqueous solution; and, optionally,
e) redissolving the separated precipitate into an aqueous solution of amino acid and phosphate;
wherein the amino acid phosphate is selectively precipitated as a monophosphate of arginine or lysine.

As the skilled person will appreciate, as the invention relates to basic amino acids, the amino acid may be selected from the group consisting of arginine, lysine and histidine. Further, the amino acid may be an L-amino acid, such as L-arginine or L-lysine, which is the form most advantageously used e.g. in plant fertilizers which is also produced by cultured bacteria.

In one embodiment, the phosphate is an arginine monophosphate, and the phosphoric acid is then added at an approximately equimolar amount of 1:1 to the concentration of arginine in the solution provided in step a). Using different molar ratios of phosphoric acid:amino acid may be used to obtain other phosphates than the monophosphate.

In step b), the combination of phosphoric acid with the aqueous solution may be performed as traditionally advised when acids are used by following the principle of "acid to base", i.e. by titering the phosphoric acid into the aqueous solution. However, the present inventors have surprisingly found that by using the reverse procedure, i.e. by titering the aqueous solution into the phosphoric acid, crystals of unexpectedly high purity could rapidly be obtained. This is described further in Example 5 below. Furthermore, by using the "base to acid" principle, the heat generated in the resulting exothermic reaction could be utilized instead of external heating, providing a very efficient process in terms of resources.

As the skilled person will appreciate, the pH will be set to an appropriate value depending on the specific amino acid separated. Thus, the method may be a multistep process where firstly, one amino acid is selectively precipitated as its monophosphate at a first pH, and secondly, the solution is adjusted to a second pH at which a second amino acid is selectively precipitated.

The invention may be utilized to obtain a highly purified amino acid, in which case step e) is performed to redissolve the precipitated amino acid phosphate after removal thereof from the original solution, followed by removal of the phosphate by any conventional method such as liquid chromatography or precipitation.

Alternatively, the present invention may be utilized to obtain a phosphate such as a monophosphate of arginine or lysine, which find subsequent use e.g. as plant fertilizers.

In order to optimize the utilization of the content of arginine or lysine in an aqueous solution which comprises amino acids as well as proteins and/or protein decomposition products, the present inventors have found that the above described method of precipitation may successfully be followed by one or more steps of adding at least one zeolite to the aqueous solution from which arginine or lysine monophosphate has been precipitated. Such further step(s) enables to recover a larger proportion of arginine or lysine from the aqueous solution than the precipitation as such, as will be discussed in more detail in the experimental part below.

Thus, the present invention also relates to a method of recovering basic amino acids such as arginine or lysine from a complex solution, which method comprises at least the steps of
a) providing an aqueous solution comprising amino acids as well as proteins and/or protein decomposition products;
b) combining the aqueous solution with phosphoric acid;
c) maintaining the aqueous solution including phosphoric acid at room temperature until a precipitate of arginine or lysine monophosphate is obtained;
d) separating arginine or lysine monophosphate from the aqueous solution;

e) optionally, redissolving the separated precipitate into an aqueous solution of amino acid and phosphate; and f) combining the aqueous solution separated in step d) with at least one zeolite under conditions allowing for adsorption of arginine or lysine to the zeolite(s).

The conditions for adsorption of basic L-amino acids to zeolites has been described in WO 2017/222464, from which the skilled person may use teachings with regard to the zeolite step(s) in the design of a multistep process wherein a precipitation of arginine is followed by adsorption of remaining arginine or lysine to at least one zeolite having the appropriate properties. Additional zeolite adsorption steps may be performed on any liquid resulting from step f), optionally using zeolite(s) having properties different from those used in the preceding adsorption step.

Various liquids may be utilized as the source of basic amino acid, as will be discussed in more detail below.

One aspect of the present invention is the selective separation of basic amino acid such as arginine or lysine from the liquid in which it was produced. Thus, the aqueous solution provided in step a) may be a broth originating from the fermentation of cells producing proteins, peptides and/or amino acids in an undefined growth medium, such as LB medium or any other composition. Such a medium will commonly include a large number of components such as sugars and nutrients added for growth as well as various other products expressed by the cells, which will require removal by separate purification steps in the conventional biotechnological manufacture of amino acids. Thus, in this aspect, the method according to the invention will include step e) wherein the amino acid phosphate precipitation is redissolved to separate the amino acid from the phosphate. As the skilled person will appreciate, an additional step of conventional separation of amino acids from phosphate may be required.

In one embodiment, the cells are bacterial strains selected from the group consisting of *Escherichia*, *Corynebacterium*, and *Agrobacterium*.

As discussed in the Background section above, the currently available methods for separating amino acids from fermentation broths are resource-demanding multistep methods for purification such as several liquid chromatography steps which may be avoided and replaced by the precipitation as phosphate according to the invention.

Thus, the present aspect enables more efficient production of amino acids than conventionally used purification protocols.

Further, this aspect may be used to produce amino acid phosphates for subsequent use in the manufacture of plant fertilizers. As amino acids are common products in most protein expression, this aspect allows for an efficient utilization of broths from which e.g. proteins have been recovered as the primary targets.

In another aspect, the aqueous solution provided in step a) is a liquid originating from hydrolysis of animal or vegetable matter. A source of commercial interest is a solution originating from the hydrolysis of feather. Feathers are readily available as by-product from poultry slaughterhouses, and contain 85%-90% keratin. Hydrolysis of keratin is frequently used, wherein the disulphide bonds and peptide bonds are broken to form smaller proteins, peptides and amino acids. However, the conventional industrial is feather protein processing method is thermal pressure hydrolysis, which requires further processing using chromatography and other purification techniques to obtain amino acids of high purity. Thus, the present invention presents an advantageous alternative to recover amino acids from the feather industry.

Like the first aspect, highly purified amino acids or as well as amino acid phosphates may be obtained.

In yet another aspect, the aqueous solution provided in step a) is a rest stream originating from pulp manufacture. The term "pulp" is used herein for a lignocellulosic fibrous material prepared by chemically or mechanically separating cellulose fibres from wood, fibre crops, waste paper, or rags. The rest streams originating from pulp mills are highly complex solutions which may include lignin and cellulose as well as various chemicals.

Depending on the contents on the stream, a preceding step of filtering the solution may be included. Like the first aspect, highly purified basic amino acids or as well as amino acid monophosphates may be obtained from this solution.

As discussed above, the method according to the invention may be used to produce a basic amino acid phosphate such as arginine monophosphate or lysine monophosphate which is subsequently combined with one or more nutrients to form a plant fertilizer.

The method according to the invention may also include a step of granulating the precipitated arginine or lysine monophosphate to obtain a format suitable for its use in solid fertilizer compositions.

Further, the method according to the invention may comprise a step of formulating a fertilizer by combining arginine or lysine monophosphate precipitated as described above with at least one binder and optionally one or more additional nutrients to form a plant fertilizer. Binders suitable for the use with arginine or lysine monophosphate in fertilizer compositions are discussed in WO 2017/200468.

The present invention also relates to a fertilizer composition which includes arginine or lysine monophosphate precipitated as described above, optionally in combination with at least one binder and/or one or more additional nutrients. Such a fertilizer may be a solid composition, such as a granulate.

Finally, the invention relates to a solid fertilizer composition which comprises arginine or lysine monophosphate, optionally in a granulate with a suitable binder, and at least one zeolite to which arginine or lysine has been adsorbed. The relative proportions of the two components (arginine or lysine monophosphate and zeolite(s)) may be varied and decided for each specific formulation based on the desired properties of the fertilizer, such as release rate.

DETAILED DESCRIPTION OF THE DRAWINGS

Figures 1, 1A, 1B, 1C:
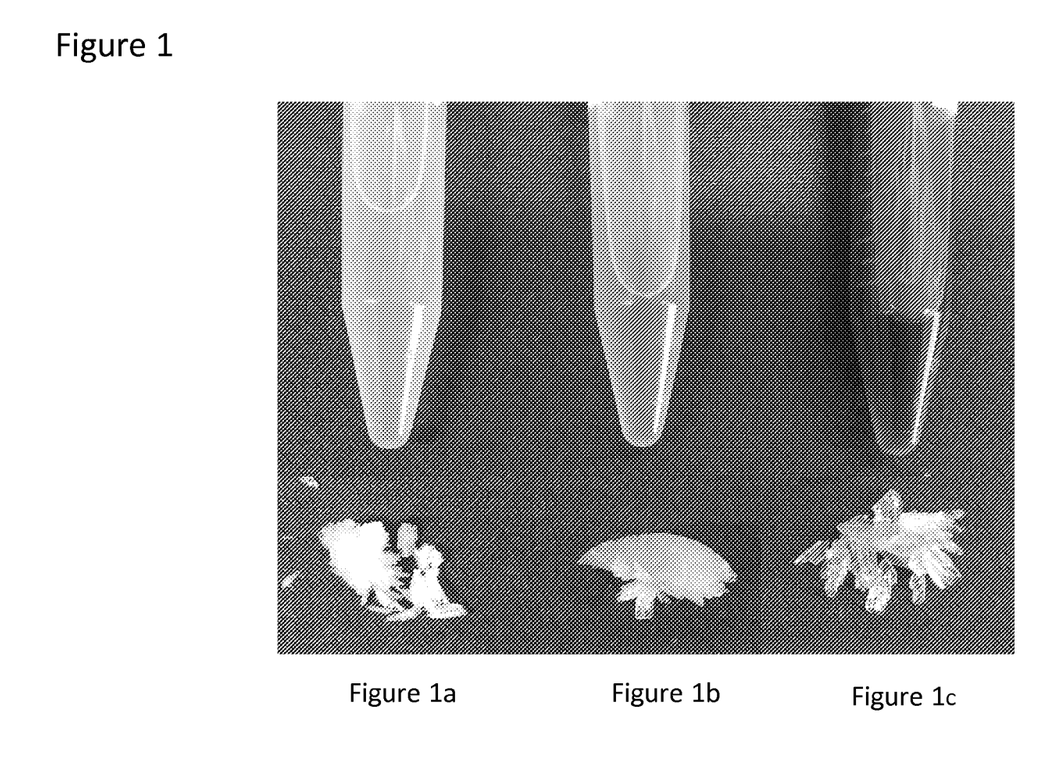

FIG. 1 is a photograph of three arginine monophosphate crystal derived according to the invention from three different fermentation broths: *Agrobacterium* (FIG. 1*a*) and *E. coli* (FIG. 1*b*) spiked with 100 g/L of arginine to simulate broths from arginine-overproducing strains; as well as a modified fermentation broth from arginine-overproducing *Corynebacterium* (FIG. 1*c*) with an arginine concentration of 300 g/L treated with an equimolar amount of phosphoric acid (1.72 mole arginine/1.72 mole phosphoric acid) and left at room temperature for 5 days. Arginine monophosphate crystals were formed during this period and retrieved from the solution. In this example, 75% orthophosphoric acid was used. As appears from visual inspection, the crystals have a very high purity.

FIG. 2 shows gas chromatograms obtained by performing gas chromatography following well established protocols on monophosphates produced according to the invention, as described in the experimental part below.

Figure 2A:
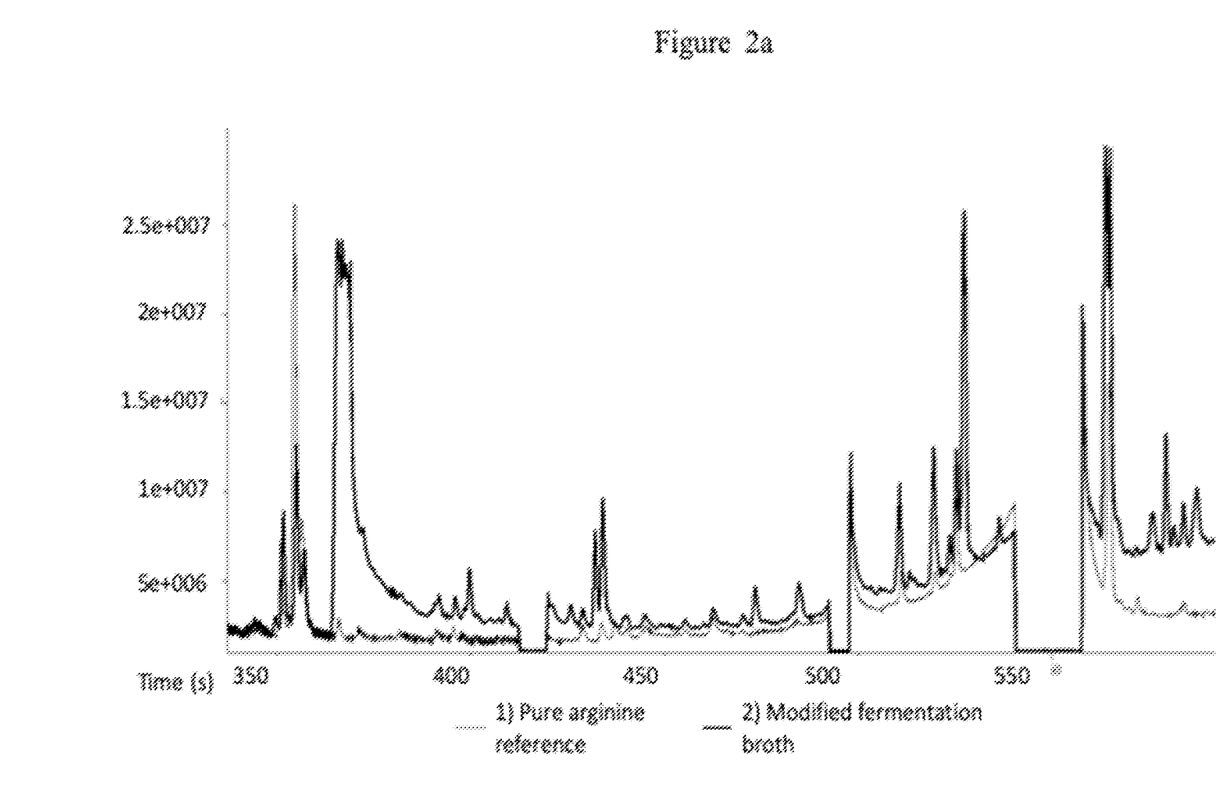
FIGS. 2a, b and c are gas chromatograms of monophosphates produced according to the invention, as described in the experimental part below.

More specifically, FIG. 2a is a gas chromatogram of 1) a pure arginine reference, 2) a modified fermentation broth. Arginine peaks were masked at 412-422 s, 492-497 s and 540-555 s in order to increase sensitivity to non-arginine content. A peak at 597 s is derived from the pure arginine reference. Numerous peaks (for example at 323 s, 365 s, 391 s, 395 s, 400 s, 432 s, 434 s, 473 s, 510 s, 519 s, 523 s, 525 s, 527 s, 535 s, 575 s, 575 s, 579 s, 581 s, 583 s and 587 s) in chromatogram 2 are reduced in amplitude or not evident in chromatogram 1 indicating an expected composition complexity in the fermentation broth not present in the pure arginine reference.

Figure 2B:
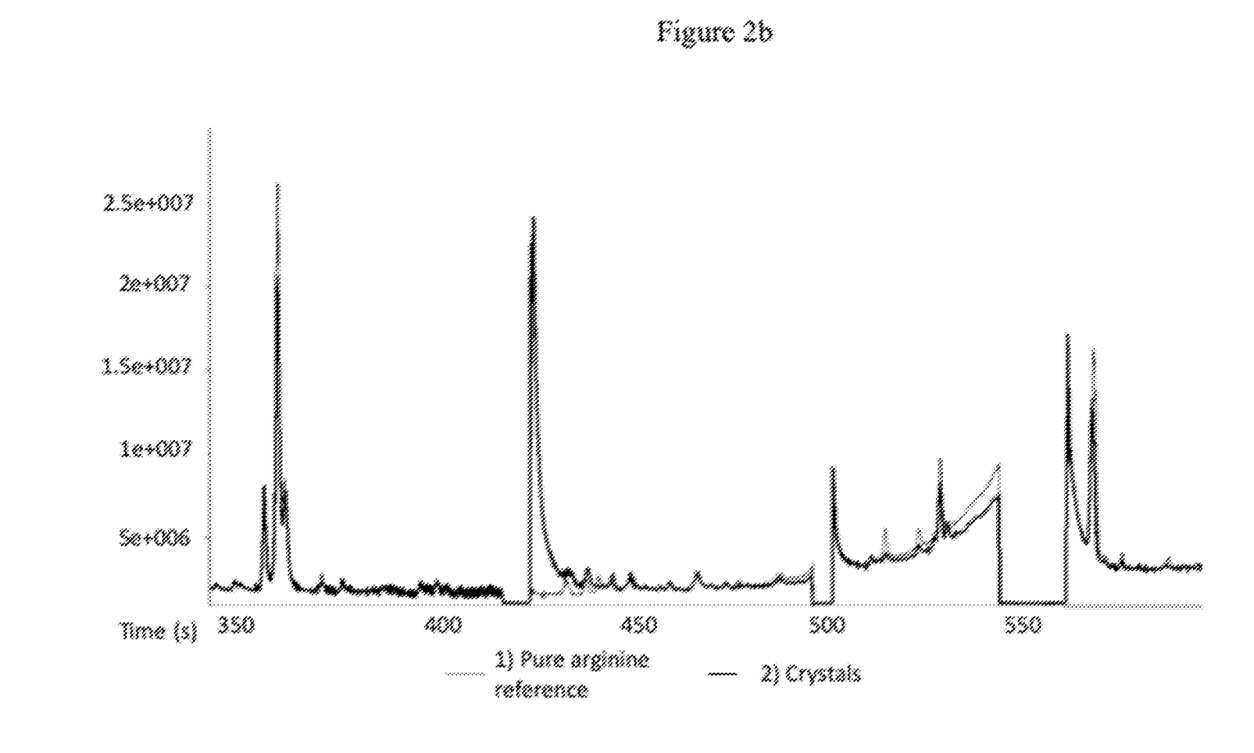

FIG. 2b is a gas chromatogram of 1) a pure arginine reference solution and 2) arginine monophosphate crystals derived from the modified fermentation broth by way of the method described herein. Arginine peaks were masked at 412-422 s, 492-497 s and 540-555 s in order to increase sensitivity to non-arginine content. The phosphate content of the crystals is evident in chromatogram 2 at ca. 421 s. Besides the extra peak from phosphate the two chromatograms are very similar indicating arginine phosphate crystals have a high level of purity.

Figure 2C:
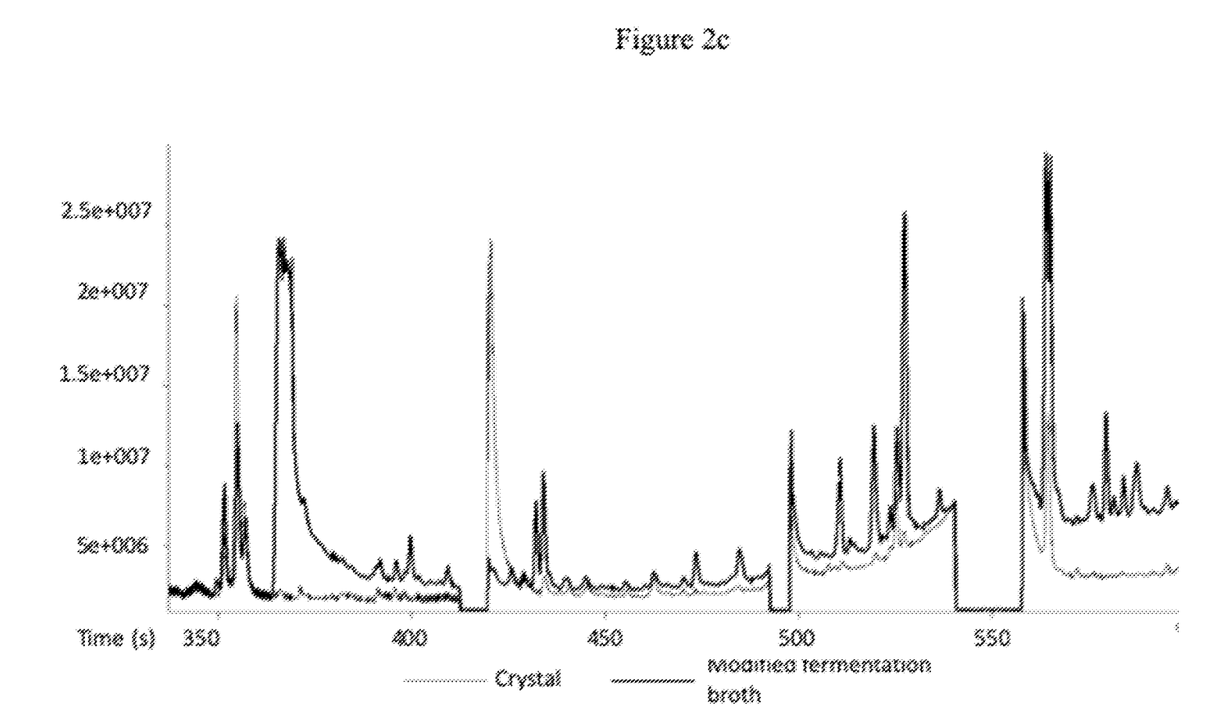

FIG. 2c is a gas chromatogram of 1) crystals precipitated from solution made from arginine phosphate crystals derived from the fermentation broth vs 2) a modified fermentation broth solution. Arginine peaks were masked at 412-422 s, 492-497 s and 540-555 s in order to increase sensitivity to non-arginine content. The phosphate content of the crystals is evident in chromatogram 3 at ca. 421 s. Numerous peaks (for example at 323 s, 365 s, 391 s, 395 s, 400 s, 432 s, 434 s, 473 s, 510 s, 519 s, 523 s, 525 s, 527 s, 535 s, 575 s, 575 s, 579 s, 581 s, 583 s and 587 s) in chromatogram 2 are reduced in amplitude or not evident in chromatogram 1 indicating a purification step has taken place by adding phosphoric acid at equimolar concentrations to the arginine content and precipitating crystals from a complex solution.

Figure 3A:
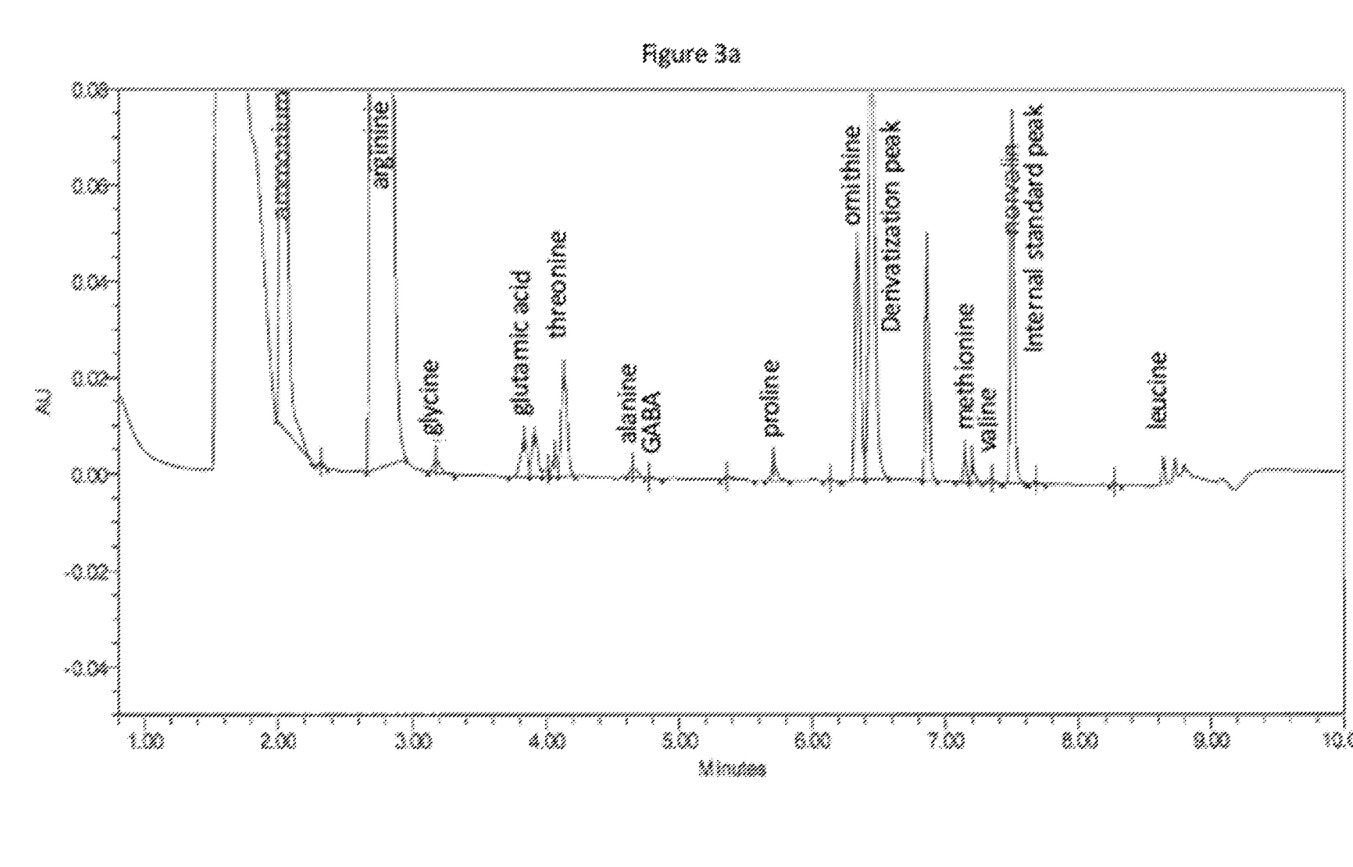
FIGS. 3a and b are chromatograms of a) a modified fermentation broth, and b) solubilized arginine phosphate crystals derived from the modified fermentation broth, respectively.
Figure 3B:
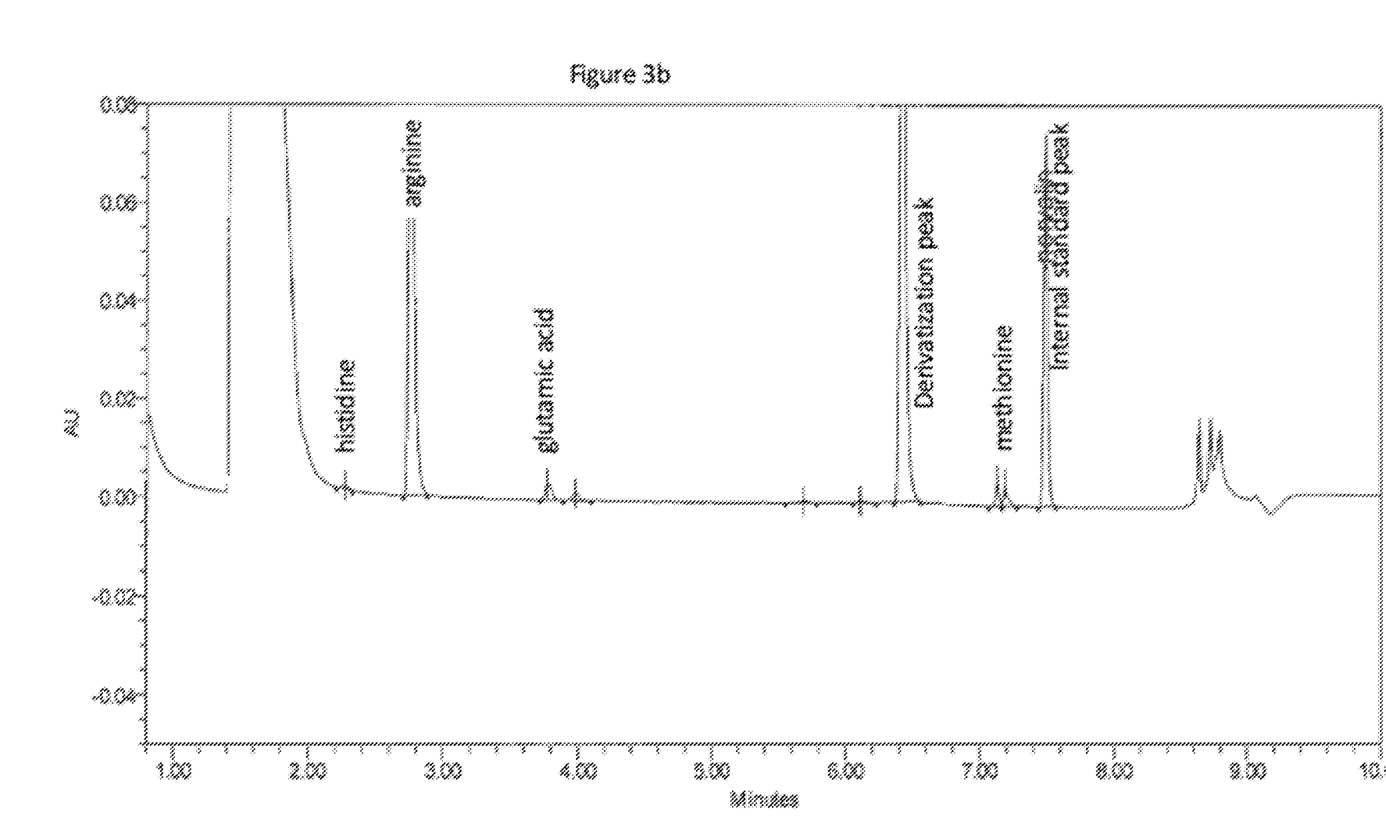

FIG. 3 are chromatograms of a) a modified fermentation broth, and b) solubilized arginine phosphate crystals derived from the modified fermentation broth, respectively. More specifically, in FIG. 3a, the peak at 1.6 min represents derivation residues, 2.2 ammonium, 2.8 arginine, 3.1 glycine, 3.9 glutamic acid, 4.1 threonine, 4.6 alanine 4.7 GABA, 5.3 proline, 6.3 ornithine, 6.7 not assign, 7.2 methionine, 7.6 novalin (internal standard), 8.3 leucin. In FIG. 3b, several peaks are reduced in amplitude or not present at all, indicating that impurities in the fermentation broth were removed during the formation of the arginine phosphate crystals.

Figure 4A:
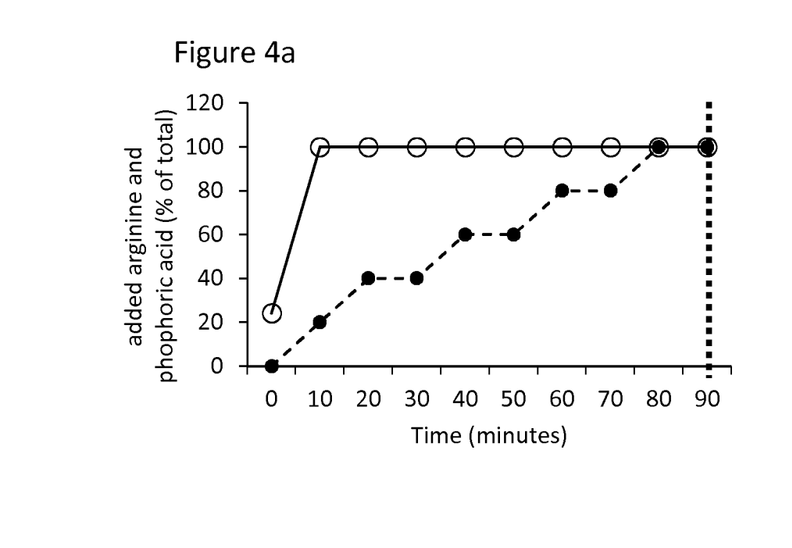
FIGS. 4a and b illustrate the reaction time of a method according to the invention when acid is added to base.
Figure 4B:
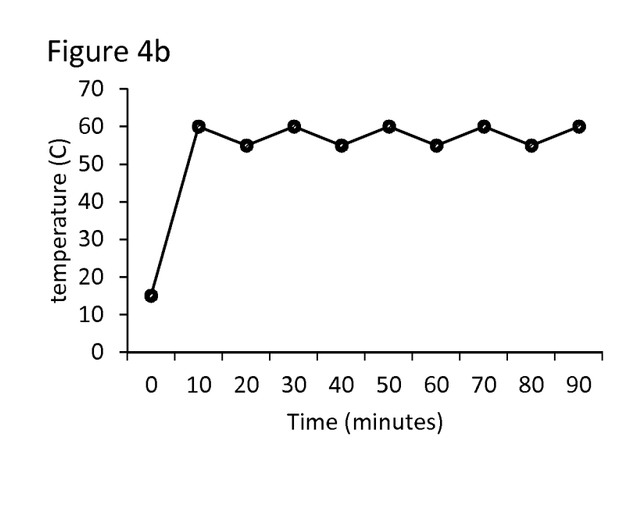

FIG. 4 is an illustration of the reaction time of a method according to the invention when acid is added to base. More specifically, FIG. 4a illustrates Method 1, wherein arginine base was dissolved in 500 ml, 60° C. dH$_2$O. The arginine solution was stirred and 75% phosphoric acid (giving an arginine to phosphate ratio of 1:1) was titered into the arginine solution at a rate in which the temperature was not allowed to exceed 60° C. (FIG. 4b). The vertical dotted line in FIG. 4a indicates the time for full mixing of arginine and phosphoric acid.

Figure 5A:
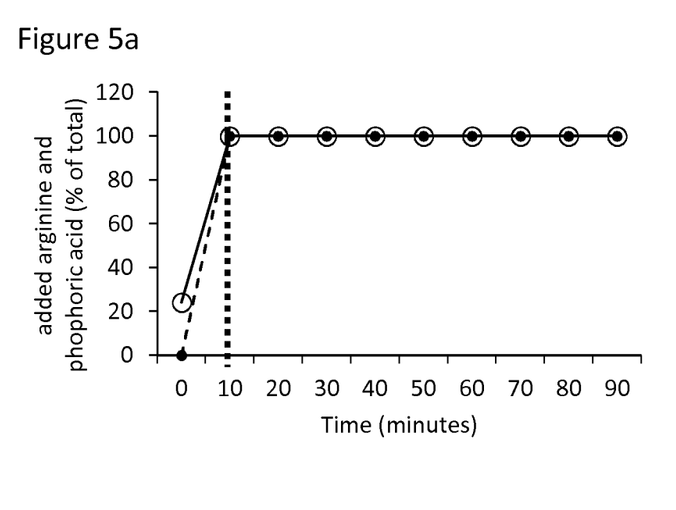
FIGS. 5a and b illustrate the reaction time of a method according to the invention when base is added to acid.
Figure 5B:
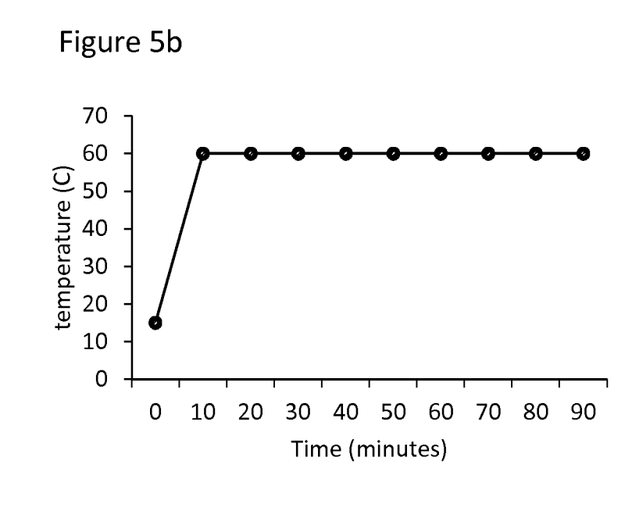

FIG. 5 is an illustration of the reaction time of a method according to the invention when base is added to acid. More specifically, FIG. 5a illustrates Method 2, wherein a slurry of only partially dissolved arginine base in 15° C. dH$_2$O (62.5 g dissolved and 187.5 g as an undissolved. The arginine solution was titered into a solution of 75% phosphoric acid with stirring at a rate so that the temperature was not allowed to exceed 60° C. until complete mixing of arginine and phosphoric acid was achieved (FIG. 5b). The vertical dotted line in FIG. 5a indicates the time for full mixing of arginine and phosphoric acid.

Figure 6:
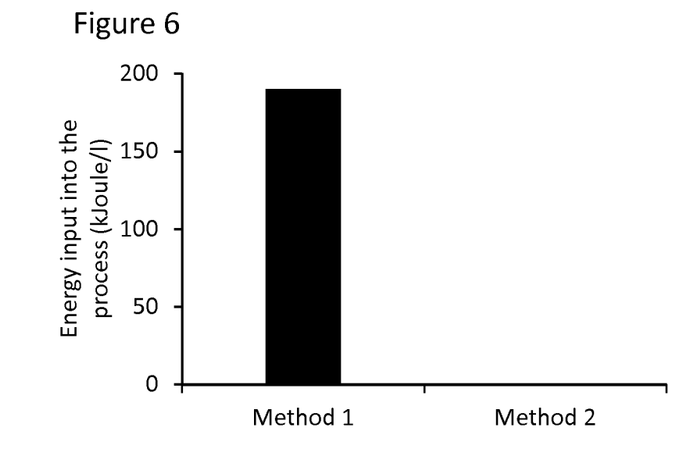
FIG. 6 illustrates the energy used for heating of water in the two methods of FIGS. 5 and 6, respectively.

FIG. 6 illustrates the energy used for heating of water in the two methods of FIGS. 5 and 6, respectively. More specifically, Method 1, which utilizes the traditional sequence of "add acid to water (Add the Acid)", uses almost 200 kJoule/litre; while the energy consumption of the less frequently used sequence of "add water to acid" is close to zero thanks to the utilization of the exothermic heat.

Figure 7A:
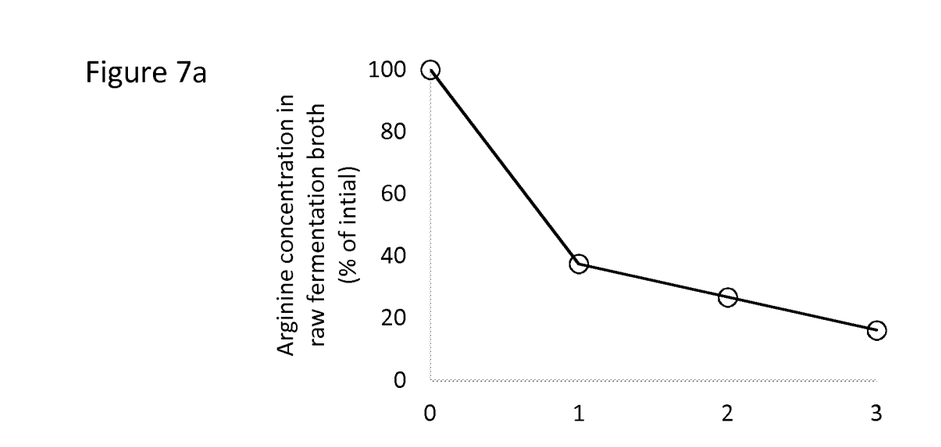
FIGS. 7a and b illustrate the arginine recovery obtainable from raw *E. coli* fermentation broth following the method described in Example 6.

FIG. 7 illustrates the arginine recovery obtainable from raw *E. coli* fermentation broth following the method described in Example 6, i.e. repeated steps of recovery through crystallization followed by addition of zeolites. More specifically, FIG. 7a shows the arginine concentration remaining in raw fermentation broth (% of initial solution concentration corresponding to 140 g arginine/l) after arginine crystallization using phosphoric acid (1), treatment of fermentation broth using zeolites (2) and repeated treatment of fermentation broth using zeolites (3).

FIG. 7a illustrates the recovery of arginine as described above, i.e. from raw fermentation broth (% of initial amount corresponding to 140 g arginine/l) after arginine crystallization using phosphoric acid (1), treatment of fermentation broth using zeolites (2) and repeated treatment of fermentation broth using zeolites (3).

EXPERIMENTAL

The present examples are provided herein for illustrative purposes only, and are not intended to be limiting the present invention as defined by the appended claims. All references provided below and elsewhere in the present application are hereby included herein via reference.

Example 1

A fermentation broth produced from an arginine-overproducing *Corynebacterium* with an arginine concentration of 300 g/L was treated with an equimolar amount (1.72 mole arginine/1.72 mole phosphoric acid) of phosphoric acid (75% orthophosphoric acid) and left at room temperature for 5 days. Arginine monophosphate crystals were formed during this period and retrieved from the solution. The crystals were analysed with Gas Chromatography-Mass Spectrometry for contaminants of other compounds other than arginine and phosphate and the impurities were found to comprise less than 0.01% of the total mass. FIGS. 1 and 2.

Example 2

A fermentation broth with *E. coli* was spiked with arginine to a concentration of 100 g/L to simulate an arginine-overproducing strain of the bacteria. The arginine-spiked broth was treated with equimolar amounts (0.57 mole arginine/0.57 mole phosphoric acid) of phosphoric acid (75% orthophosphoric acid) and left at room temperature for 5 days. Arginine phosphate crystals were formed during this period and retrieved from the solution. The crystals were analysed with Gas Chromatography-Mass Spectrometry for contaminates of other compounds than arginine and phosphate and the impurities were found to comprise less than 0.01% of the total mass. FIG. 1.

Example 3

A fermentation broth with *Agrobacterium* was spiked with arginine to a concentration of 100 g/L to simulate a arginine overproducing strain of the bacteria. The arginine spiked broth was treated with equimolar amounts (0.57 mole arginine/0.57 mole phosphoric acid) of phosphoric acid (75% orthophosphoric acid) and left at room temperature for 5 days. Arginine phosphate crystals were formed during this period and retrieved from the solution. The crystals were analysed with Gas Chromatography-Mass Spectrometry for contaminates of other compounds than arginine and phosphate and the impurities were found to comprise less than 0.01% of the total mass. FIG. 1.

Example 4

A fermentation broth with *E. coli* was spiked with L-arginine to a concentration of 140 g/L to simulate a fermentation broth from an arginine overproducing strain of the bacteria. The arginine spiked broth was treated with equimolar amounts of phosphoric acid (0.80 mole arginine/0.80 mole phosphoric acid) and left at room temperature for 5 days. Arginine phosphate crystals were formed during this period and retrieved from the solution. The modified fermentation broth and crystals was analysed with Ultra Performance Liquid Chromatography for ammonium and amino acid composition. A number of compounds that were present in the fermentation broth for example ammonium, glycine, threonine, alanine, GABA, proline, ornithine, valine and leucine were not present in the solubilized crystal solution. Impurities were found to comprise less than 0.01% of the total mass in the crystal, see FIGS. 3*a* and 3*b*.

Example 5

Arginine phosphate crystals were produced from complex solutions, and the two alternative procedures of the invention were compared.

In the first procedure, sometimes referred to as an "acid to base" method, 250 g of arginine base (CAS: 74-79-3) was dissolved in 500 ml, 60° C. dH$_2$O. The arginine solution was stirred and 119 ml of 75% phosphoric acid (arginine/phosphate 1:1) was titered into the arginine solution at a rate were the temperature was not allowed to exceed 60° C. It is well known that heating of arginine solutions above 60° C. will lead to the breakdown of arginine into ornithine and ammonium. The time for completing the mixing of arginine and phosphoric acid was measured, see FIGS. 4*a* and *b*.

The alternative procedure, sometimes referred to as a "base to acid" method, was set up as follows: 250 g of arginine base was partly dissolved in 15° C. dH$_2$O 62.5 g dissolved and 187.5 g as an undissolved. Instead of titering the acid into the base, a reverse procedure was used in which the arginine slurry was titered into 119 ml of 75% phosphoric acid with stirring at a rate were the temperature was not allowed to exceed 60° C. Due to the exothermal reaction, the temperature increases from 15° C. to 60° C. and concomitantly, the solubility for arginine increases from 131.3 g/l at 15° C. to 544 g/l at 60° C. allowing for 100% solubilization of arginine, see FIGS. 5*a* and *b*. The time for complete mixing of arginine and phosphoric acid was measured. By following the alternative procedure of mixing partly undissolved arginine directly into 75% phosphoric acid, the time to complete mixing of arginine and phosphoric acid could be reduced 8.8 times, and no extra energy for heating was required, see FIG. 6.

When using the "acid to base" method, the rate of phosphoric acid incorporation will be strictly limited by the exotherm that risks leading to degradation of arginine if the temperature exceeds 60° C. The energy requirement in the first procedure was 190 kJoule/1 for heating water from 15 to 60° C., see FIG. 6, Method 1. In the alternative method, energy for heating of the arginine solution was provided by the exothermal reaction when the arginine slurry was added into phosphoric acid, and hence no energy for heating was required, see FIG. 6, Method 2.

Example 6

The present example was set up to illustrate how the present invention may be utilized in process to produce pure arginine phosphate crystals from complex solutions with high recovery.

Materials and Methods

Arginine was incorporated into zeolites as follows: 21.5 g of *Clinoptilolite* natural zeolite 1-3 mm (CAS: 12173-10-3) was loaded with arginine from 100 ml *E. coli* fermentation broth containing 52.5 g/l arginine. The solutions remaining after zeolite treatment were analysed on an UPLC for arginine concentration. The treatment was repeated 2 times.

Analysis of ammonium and amino acids was analysed as follows: Analysis by reversed-phase liquid chromatography using Waters Ultra High Performance (UPLC) system with a Waters Tunable UV (TUV) detector.

Derivatization of samples were made with Waters AccQ-Tag Ultra Derivatization kit for amino acid analysis, as described by Inselsbacher et al. 2011.

(Exception; instead of 10 µl internal standard, here 20 µl standard was used) 10 µl sample was added to 70 µl borate buffer (1M), 20 µl internal standard (nor-valine, 100 µmole N/1) after which 20 µl of AccQ-Tag derivatization reagent was added and thoroughly mixed immediately and subsequently heated to 55° C. for 10 mm.

Amino acids were determined after separation on an AccQ-Tag Ultra column by elution with a mixture of 99.9% formic acid and 10% acetonitrile at the following gradient 0-5.74 min isocratic 99.9% formic acid, declining to 90.9% formic acid from 5.74 min to 7.74 min, to 78.8% formic acid at 8.24 min and then to 40.4% formic acid at 8.74 min, before re-equilibration with 99.9% formic acid from 8.74 to 9.54 min. The flow rate was 0.6 ml/min and the column temperature was set to 55° C.

Experimental Procedure

Figure 7B:
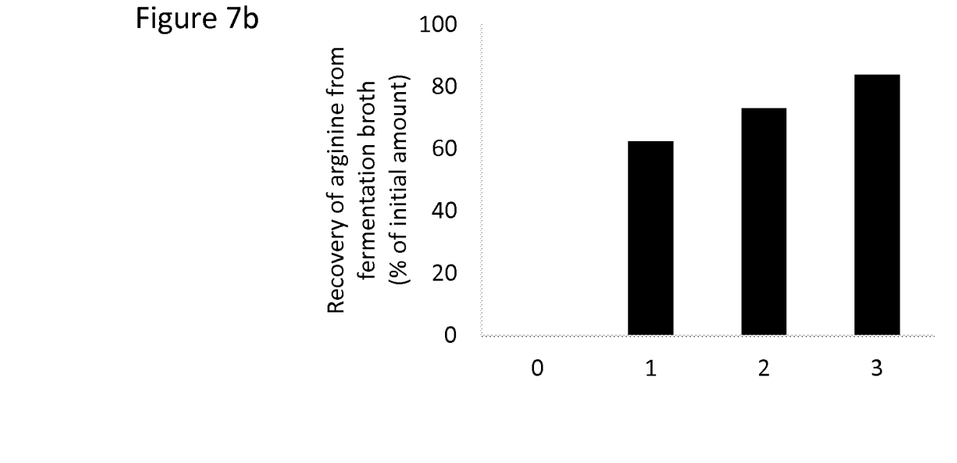

A fermentation broth with *E. coli* was spiked with arginine to a concentration of 140 g/L to simulate a arginine overproducing strain of the bacteria. The arginine spiked broth was treated with equimolar amounts of phosphoric acid (0.80 mole arginine/0.80 mole phosphoric acid) and left at room temperature for 5 days. Arginine phosphate crystals were formed during this period and retrieved from the solution. The concentration of arginine in the fermentation broth after crystallization was 52.5 g/L. 21.5 g of *Clinoptilolite* natural zeolite of diameter 1-3 mm was added to this solution. The arginine concentration was measured after the zeolite addition and the arginine concentration in the fermentation broth was found to be 37.5 g/L. The zeolite treatment was repeated resulting in an arginine concentration of 22.5 g/L in the fermentation broth. The total recovery of arginine from the fermentation broth after these steps was 84%, see FIGS. 7*a* and *b*.

The invention claimed is:

1. A method of separating arginine or lysine from an aqueous solution, which method comprises
   a) providing an aqueous solution comprising amino acids as well as proteins and/or protein decomposition products;
   b) combining the aqueous solution with phosphoric acid;

c) maintaining the aqueous solution including phosphoric acid at room temperature until a precipitate of amino acid phosphate is obtained, wherein the amino acid phosphate is selectively precipitated as a monophosphate of arginine or lysine;
d) separating said precipitate from the aqueous solution; and
e) redissolving the separated precipitate into an aqueous solution of amino acid and phosphate.

2. A method according to claim 1, wherein the amino acids comprise L-arginine.

3. A method according to claim 1 or 2, wherein the amino acid phosphate precipitated is a monophosphate in crystalline form.

4. A method according to claim 1 or 2, which includes a step of determining, in the solution provided in step a), the concentration of free amino acid which is to be precipitated as its monophosphate.

5. A method according to claim 1, wherein the phosphoric acid is combined with the aqueous solution in an approximately equimolar ratio to the amino acid concentration of the aqueous solution.

6. A method according to claim 1, wherein step b) is performed by adding the aqueous solution to the phosphoric acid.

7. A method according to claim 1, wherein the aqueous solution provided in step a) is a cell fermentation broth.

8. A method according to claim 7, wherein the cell fermentation broth is a microorganism fermentation broth.

9. A method according to claim 8, wherein the microorganism is selected from the group consisting of *Escherichia*, *Corynebacterium*, and *Agrobacterium*.

10. A method according to claim 1, wherein the aqueous solution provided in step a) is animal or vegetable matter hydrolysis liquid.

11. A method according to claim 1, wherein said solution provided in step a) is feather hydrolysis liquid.

12. A method according to claim 1, wherein the aqueous solution provided in step a) is a pulp manufacture rest liquid.

13. A method according to claim 1, which includes a preceding step of filtering the solution provided in step a).

14. A method according to claim 7, wherein the cell fermentation broth is a bacteria fermentation broth.

15. A method according to claim 1, wherein said solution provided in step a) comprises keratin hydrolysis liquid.

16. A method according to claim 1, wherein said solution provided in step a) comprises lignin and cellulose.

* * * * *